(12) United States Patent
Odedra

(10) Patent No.: US 7,133,782 B2
(45) Date of Patent: Nov. 7, 2006

(54) SEQUENCING METHOD AND APPARATUS

(75) Inventor: Raj Odedra, Amersham (GB)

(73) Assignee: GE Healthcare UK Limited, Amersham (GB)

(*) Notice: Subject to any disclaimer, the term of this patent is extended or adjusted under 35 U.S.C. 154(b) by 477 days.

(21) Appl. No.: 10/312,048

(22) PCT Filed: Jul. 2, 2001

(86) PCT No.: PCT/GB01/02985

§ 371 (c)(1),
(2), (4) Date: Mar. 25, 2003

(87) PCT Pub. No.: WO02/03305

PCT Pub. Date: Jan. 10, 2002

(65) Prior Publication Data

US 2003/0186276 A1    Oct. 2, 2003

(30) Foreign Application Priority Data

Jul. 5, 2000    (GB) .................................... 0016472

(51) Int. Cl.
G06F 19/00    (2006.01)
C12Q 1/68    (2006.01)

(52) U.S. Cl. ........................................... 702/20; 435/6

(58) Field of Classification Search ..................... None
See application file for complete search history.

(56) References Cited

U.S. PATENT DOCUMENTS 5,302,509 A  *  4/1994  Cheeseman .................... 435/6
5,552,278 A     9/1996  Brenner

FOREIGN PATENT DOCUMENTS

| WO | WO 91/06678 | * | 5/1991 |
| WO | WO 93/05183 | | 3/1993 |
| WO | WO 93/21340 | | 10/1993 |

* cited by examiner

Primary Examiner—John S. Brusca
(74) Attorney, Agent, or Firm—Yonggang Ji

(57) ABSTRACT

In a method of identifying an unknown nucleotide sequence using base addition, a sequence of bases is obtained from a template, a base in the sequence is identified as an unknown base, an "unknown" indicator is included in the sequence, and an output sequence is generated containing the unknown base indicator. The sequence of bases is obtained from the template by evaluation of a reporter and assigning the bases in accordance therewith. A determination is made as to whether the reporter is from a preceding cycle of base determination, and if the reporter is from a preceding cycle of base determination, the base assignation is discarded.

15 Claims, 1 Drawing Sheet

SEQUENCE LISTING

```
<160> NUMBER OF SEQ ID NOS: 7
<210> SEQ ID NO 1
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 1
gatcggctga ccatggac                                                 18

<210> SEQ ID NO 2
```

```
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 2
gatcggctga ccatggaccc tgacagt                                    27

<210> SEQ ID NO 3
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 3
gatcggctga ccatggacct ctgacagt                                   28

<210> SEQ ID NO 4
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 4
gatcggctga ccatggacct ctgacagt                                   28

<210> SEQ ID NO 5
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 5
gatcggctga ccatggacct ctgacagt                                   28

<210> SEQ ID NO 6
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 6
gatcggctga ccatggcctc tgacagt                                    27

<210> SEQ ID NO 7
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 7
gatcggctga ccatggacct ctgacagt                                   28
```

SEQUENCING METHOD AND APPARATUS

FIELD OF THE INVENTION

The present invention relates to a sequencing method and apparatus that permits error correction during the sequencing of individual molecules.

BACKGROUND OF THE INVENTION

Sequencing is routinely performed by the method of chain termination and gel separation, essentially as described by Sanger, F., S. Nicklen, and A. Coulson (Proc Natl Acad Sci USA, 1977. 74(12); p. 5463–7). The method relies on the generation of a mixed population of DNA fragments representing terminations at each base in the sequence. The sequence is then determined by electrophoretic separation of these fragments.

Recent efforts to increase the throughput of sequencing have resulted in the development of alternative methods that eliminate the electrophoretic separation step. A number of these methods utilise base extension (i.e. base addition) and have been described for example in WO 93/21340, U.S. Pat. Nos. 5,302,509 and 5,547,839. In these methods, the templates or primers are immobilised on a solid surface before exposure to reagents for sequencing. The immobilised molecules are incubated in the presence of nucleotide analogues that have a modification at the 3' carbon of the sugar residue that reversibly blocks the hydroxyl group at that position. The incorporation of such modified nucleotides by a polymerase ensures that only one nucleotide is added during each cycle of base extension. The added base is then detected by virtue of a label that has been incorporated into the 3' blocking group. Following detection, the blocking group is removed (or 'cleaved'), typically, by photochemical means to expose a free hydroxyl group that is available for base addition during the next cycle.

Generally, non-separation-based approaches rely on the presence of large numbers of template molecules for each target sequence to generate a consensus sequence from a given target. Thus, for example, base extension reactions may be applied to multiple templates by interrogating discrete spots of nucleic acid, each comprising a multiplicity of molecules, immobilised in a spatially addressable array.

However, reactions of terminator incorporation/cleavage, or base excision are prone to errors. For example, as described above, base extension strategies have generally utilised nucleotide analogues that combine the functions of a reporter molecule, usually a fluor, with that of a terminator occupying the 3' position on the sugar moiety. The bulky nature of the group and its position renders these compounds highly inefficient substrates for polymerases. In addition, the cleavage of the terminator group to permit subsequent additions is also subject to inefficiencies. In the presence of thousands, or preferably millions, of molecules for each target, even modest errors of less than 5% result in a cumulative loss of synchrony, between the multiplicity of strands representing each molecule, within a small number of cycles. Thus, with each cycle of sequencing the background noise increases progressively with a consequential deterioration of signal with each addition. This means that the number of bases of sequence data that can be obtained is limited before the specific signal becomes indistinguishable from background.

Recent advances in methods of single molecule detection (described, for example, in Trabesinger, W., et al., Anal Chem., 1999. 71(1); p. 279–83 and WO 00/06770) make it possible to apply sequencing strategies to single molecules. However, sequencing, when applied to clonal populations of molecules, is a stochastic process that results in some molecules undergoing reactions while others remain unmodified. Thus, in conventional sequencing methods, errors such as mis-incorporations are not normally of serious significance as the large numbers of molecules present ensure that consensus signal is obtained. When these reactions are applied to single molecules the outcomes are effectively quantized.

One such single molecule sequencing method is based on base excision and described, for example, in Hawkins, G. and L. Hoffman, Nature Biotechnology, 1997. vol.15; p.803–804 and U.S. Pat. No. 5,674,743. With this strategy, single template molecules are generated such that every base is labelled with an appropriate reporter. The template molecules are digested with exonuclease and the excised bases are monitored and identified. As these methods use highly processive enzymes such as Lambda exonuclease, there is the potential for analysing large templates of several kilobases in length. However, the continuous monitoring of excised bases from each template molecule in real time limits the number of molecules that can be analysed in parallel. In addition, there are difficulties in generating a template where every base is labelled with an appropriate reporter such that excised bases can be detected on the basis of intrinsic optical or chemical properties.

Methods based on base extension (such as BASS) have also been adapted to a single molecule approach.

However, these techniques are prone to errors. In particular, incorporation of modified nucleotides can fail, for example, as the result of decreased efficiency of polymerase action with modified nucleotides. Where the reporter molecule is a fluorescent molecule, errors can also occur through failure of fluorescence because the fluor is lost, damaged, bleached, or unexcited. At the single molecule level, failures such as these will result in a failure in obtaining adequate sequence.

It is an object of the present invention to provide a sequencing method that enables errors to be detected. It is a further object of the present invention to allow analysis and error prevention, or correction, by monitoring the fate of individual molecules through sequencing reactions.

SUMMARY OF THE INVENTION

The invention in its various aspects is defined in the independent claims below, to which reference should now be made. Advantageous features are set forth in the appendant claims.

Briefly, in a preferred embodiment of the invention which takes the form of a method of analysing a nucleotide sequence, a sequence of bases is obtained from a template, and a base in the sequence is identified as an unknown base. An 'unknown' indicator is included in the sequence at the position corresponding to the unknown base, and an output sequence is generated containing the unknown base indicator. In the preferred embodiment the sequence of bases is obtained from the template by evaluation of a reporter and assigning the bases in accordance therewith. A determination is made as to whether the reporter is from a preceding cycle of base determination, and if the reporter is from a preceding cycle of base determination, the base assignation is discarded.

The nucleotide sequence to be analysed may be an RNA or DNA sequence.

BRIEF DESCRIPTION OF THE DRAWING

The invention will now be described in more detail by way of example with reference to the accompanying drawing in which.

DETAILED DESCRIPTION OF THE PREFERRED EMBODIMENT

Figure 1:
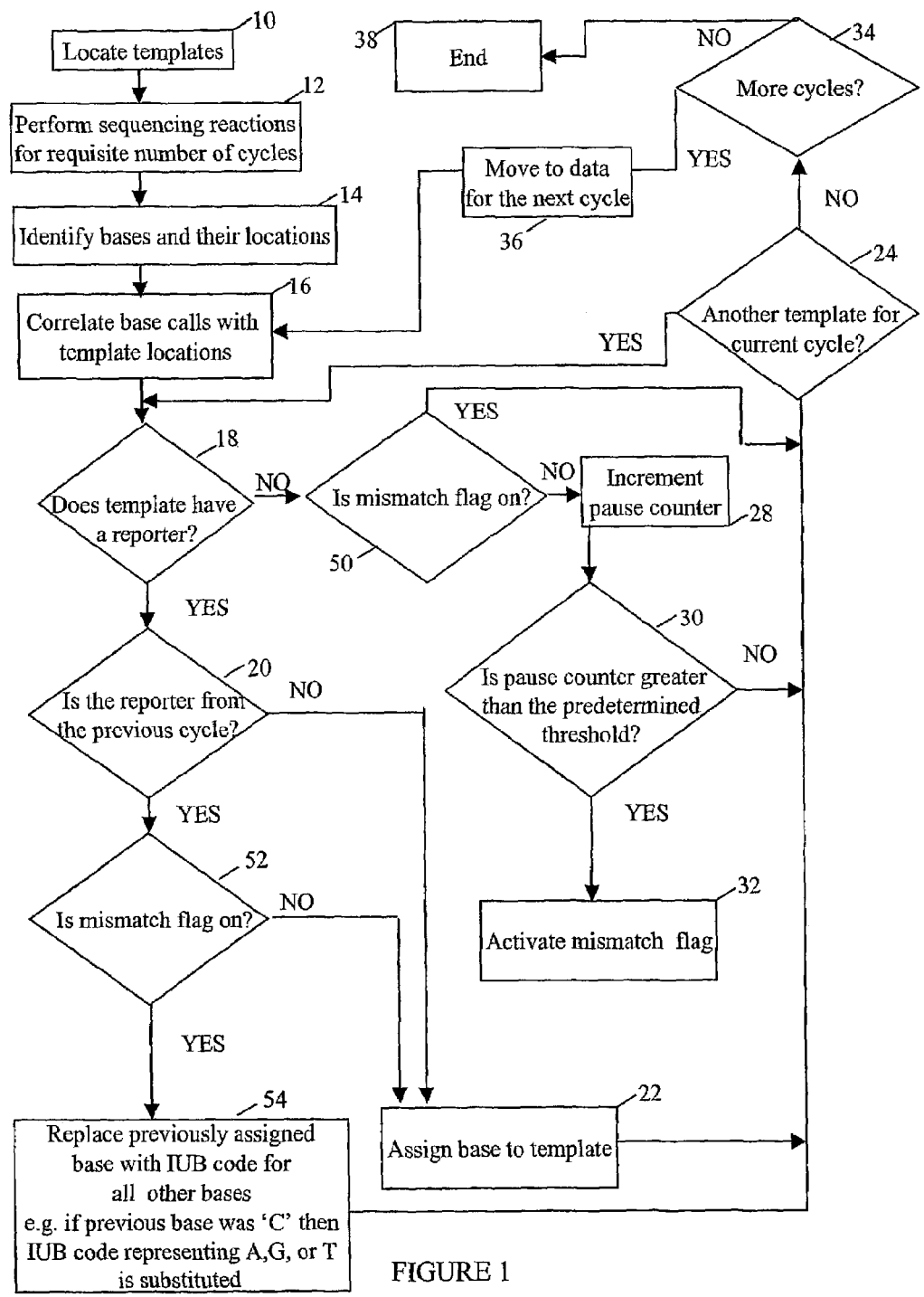
FIG. 1 is a flow chart illustrating a method of analysing data obtained during a reaction to determine the sequence of a biological molecule, such as a nucleic acid molecule, and forming a preferred embodiment of the invention.

FIG. 1 shows a flow diagram exemplifying a method of obtaining sequence information from a template. The method accounts for errors by (a) identifying bases that are carried over from a preceding cycle and (b) detecting paused molecules that may occur from failure of labelling or misincorporation of bases. The data analysis method makes use of a standard sequencing reaction which is performed as follows. First, a nucleic acid molecule for which sequence data is required, a template, is bound to a solid surface such as a microscope slide. The template can be labelled so that its position can be determined when the slide is viewed through a fluorescent microscope scanner, for example. The first base or nucleotide, i.e. A, C, G, or T, in the sequence of the template is queried by a chemical reaction adding a fluorescently-labelled base or a tag representing that base. This may be any one of A, C, G or T, or all four of them labelled with four different distinguishable labels. The first base in the template will bind to its complementary base in well-known fashion; that is A binds to T, and C binds to G, and vice versa. Base incorporation can be effected by extending the template with a polymerase enzyme or by ligating a labelled oligonucleotide with a ligase. Incorporation of the labelled base is detected and its identity determined. The label from that base is then removed. This series of steps is then repeated for the successive bases in the template.

Suitable standard sequencing reactions involving base addition/incorporation include base extension reactions such as those described in WO 93/21340, U.S. Pat. No. 5,302,509 and U.S. Pat. No. 5,547,839 and techniques such as those described in U.S. Pat. No. 5,763,175, U.S. Pat. No. 5,599,675, U.S. Pat. No. 5,856,093 and U.S. Pat. No. 5,715,330 in which successive rounds of sequencing involve base excision of the template prior to incorporation of the subsequent base.

When this sequencing reaction is performed, errors can occur. For example, (i) a base can be wrongly incorporated, that is misincorporated, or (ii) a label from one cycle can fail to be removed before the next cycle is performed, or (iii) incorporation of a base in any one cycle may fail. In the preferred embodiment of the invention to be described the data from sequence reactions is assimilated in such a way that the effects of these errors can be reduced.

Methods for deposition and fixation of molecules onto solid phases are well known in the art. Methods of attaching nucleic acids, for example, are reviewed in Schena (ed.), DNA Microarrays: A practical approach, Oxford University Press (1999) ISBN: 0199637768. Typically, the solid phase will be glass, although other materials such as amorphous or crystalline silicon or plastics can be used.

A plurality of molecules can be attached to the solid phase in an ordered array but, more preferably, they will be attached in a random manner. A random attachment of molecules may comprise any number of molecules, preferably distributed at a density appropriate for optical resolution of sequence information.

A suitable reporter moiety may be any one of various known reporting systems. It may be a radioisotope by means of which the incorporated nucleoside analogue is rendered easily detectable, for example $^{32}P$, $^{33}P$, $^{35}S$ incorporated in a phosphate or thiophosphate or H phosphonate group or alternatively $^{3}H$ or $^{14}C$ or an iodine isotope. It may be an isotope detectable by mass spectrometry or NMR. It may be a signal moiety e.g. an enzyme, hapten, fluorophore, chromophore, chemiluminescent group, Raman label, electrochemical label, or signal compound adapted for detection by mass spectrometry.

Each sequencing step will result in the attachment of reporter molecules to individual templates and the detection of the reporter moiety incorporated will permit the identity of the base to be assigned. In the case of fluorescent reporters, these molecules will then be identified by, for example, fluorescence microscopy (e.g. using a PMT or CCD) and the fluorescence property of the reporter will permit the assignment of identity to the base incorporated in the sequencing reaction.

In order to collect data from sequential rounds of sequencing cycles the template must be located. This can be achieved concurrently with the first cycle of sequencing where the reporter molecule in the first base identifies template location or the template and/or primer may itself be labelled with a reporter moiety such that its location on the solid phase may be detected in advance of the sequence cycling reaction. Knowing the location of each template molecule makes it possible to monitor the state of each molecule following all subsequent events during cycles of sequencing. Subsequent failure of addition, for example, manifests itself by lack of fluorescence at a location known to contain a template. Failure of the reporter due either to a lack of stimulus, or chemical damage can also be determined once the location of the template has been determined. These failed reactions can be tracked and treated in the final sequence as potential gaps due to reporter failure. If these molecules resume participation in subsequent cycles this, too, can be tracked and a meaningful sequence obtained. Individual points of single base gaps can be identified and, where multiple identical sequences have been arrayed onto the solid surface, a consensus sequence can be built up though comparisons with reference strands such as sequences of other copies of templates in the sequencing array. Alternatively single base gaps may be identified by comparison with a reference strand which may be the known sequence (e.g. in the application of this technique to mutation detection).

Thus we have appreciated that it is possible in this system to correct errors, particularly errors associated with single molecule sequencing. Errors that need to be corrected are failure of reporter cleavage and elimination before the next cycle, failure of incorporation, damage to reporter (e.g. damage to fluor), and misincorporation.

Once located, all sequencing cycle outcomes for the molecule located will be measurable. Using two sets of nucleotide analogues permits the identification of reporter that has been carried over from the previous cycle. The recurrence of a reporter from the previous cycle can therefore be identified and monitored.

Knowing the location of the template molecule also permits the identification of templates that appear not to have extended. As discussed above, failure to observe a reporter molecule can be due to lack of incorporation, but can also be due to damage to the reporter moiety. However, as the presence of damaged molecules can be effectively minimised by a purification process during the synthesis of modified nucleotides where breakdown products and products of side reactions can be identified and eliminated, the absence of fluorescence is therefore more likely to be a result of failure to incorporate a modified nucleotide.

If, after any cycle of sequencing, a template molecule is not associated with any reporters, the sequence is marked accordingly at this point to indicate a "pause". In the next round of sequencing, the template molecule may then be associated with a reporter i.e. the "paused" molecule resumes extension allowing sequence data to be obtained. However, the template molecule may continue to lack association with any reporters for more than one cycle, and the sequence will be marked as a pause for each respective cycle.

A positional marker generated during sequencing will be useful for interpreting gaps in alignments when comparing with the sequence generated with reference sequences or with other sequences generated during the sequencing procedure using one of the alignment algorithms known to those skilled in the art.

It is possible to predict positions of mis-incorporation knowing the inherent properties of the pertinent polymerases and ligases used. For example, it is known to those practised in the art that primer sequences that contain a mismatched terminal base are poorer templates for polymerases, with extension efficiencies of between $10^2$ to $10^6$-fold lower than matched sequences (see Huang, M., N. Arnheim, and M. Goodman, Nucleic Acids Res, 1992. 20(17): p. 4567–73., Tindall KR, K. T., Biochemistry, 1988. 27(16): p. 6008–13, Esteban, J., M. Salas, and L. Blanco, J Biol Chem, 1993. 268(4): p. 2719–26). Molecules that remain paused for several cycles, or to the end of the sequencing protocol, therefore have a much higher likelihood of containing a terminal mismatch. Templates that undergo such pauses are therefore tagged at the last base call position as potential terminations due to mismatches. Identification of the sequenced fragment is then achieved through alignment to a reference sequence or other sequenced templates from the same sample. Mismatches that occur at marked positions are more likely to be the result of mis-incorporation rather than representing the true sequence and can therefore be interpreted accordingly.

The number of cycles for which a template molecule is paused can be counted by successive detection of a lack of incorporated reporter. A threshold for the likelihood of successive pauses resulting by chance can be set during the analysis of the sequence data. The threshold above which successive pauses can be classed as resulting from a mismatch will be dependent upon the efficiency of labelling either by polymerase dependent base extension, or sequence dependent ligation. For example, if the threshold for the likelihood of successive pauses resulting by chance is set at $1\times10^{-6}$% the following numbers of pauses will be counted, taking into account different efficiencies of labelling, before the pause is counted as a mismatch.

| Efficiency of labelling by primer extension, or ligation of cohesive termmi | Number of pauses encountered before exceeding a likelihood cut off of $1 \times 10^{-6}$% |
| --- | --- |
| 99.9% | 3 |
| 99.5% | 4 |
| 99% | 4 |
| 95% | 5 |
| 90% | 6 |
| 80% | 8 |

For greater certainty, the threshold may be increased appropriately. The degree of certainty required will be dependent on the tolerance of the sequencing application; a less stringent cut off can be tolerated if the aim is simply to identify the template fragments, rather than precisely determine sequence differences. The effect of a lower efficiency of label incorporation can also be offset by the degree of sequencing redundancy. The probability of a misincorporation, in this instance, is dealt with statistically.

Imaging and locating single molecules, principally by fluorescence, is familiar to those practised in the art (see Trabesinger, W., et al., Anal Chem., 1999. 71(1): p. 279–83, Harms, G., et al., Biophys. J., 1999. 177: p. 2864–2870, Deschryver, F., Pure & Appl. Chem, 1998. 70: p. 2147–2156., Bartko, A. and R. Dickson, J Phys Chem B, 1999. 103: p. 11237–11241). Data files that contain information regarding location and type of label are, therefore, readily generated. In one embodiment of this invention, the analysis of sequence data is performed at the end of the sequencing procedure and after all the sequencing data has been acquired. This data, in one or more files, may be analysed to determine the locations of the templates and identify any attached reporters at these positions. Such data is then subjected to a second analysis to build sequences for all located templates.

Preferably, cycles of sequencing reaction and data analysis are performed concurrently. In this instance, data generated from each cycle is analysed to locate reporter molecules, these locations are then correlated with locations of the templates. The sequences for each located template can then be built on with each successive cycle.

The preferred procedure embodying the invention will now be described with reference to FIG. 1.

In the system illustrated in FIG. 1, molecules to be sequenced have been fixed onto solid phases by standard procedures as described in the art. (Reviewed in Schena (ed.), DNA Microarrays: A practical approach, Oxford University Press (1999) ISBN: 0199637768). The template, bound to a solid surface such as a microscope slide, is labelled so its position can be determined when the slide is viewed through a fluorescent microscope scanner, for example. At step 10, a relevant template is first located.

Sequencing reactions involving base incorporation which can be effected by extending the template with a polymerase enzyme or by ligating a labelled oligonucleotide with a ligase are now performed, step 12.

As described above, the sequencing step will result in the attachment of a reporter molecule to the first base in the sequence of the template, and the detection of the reporter moiety which is incorporated permits the identity of the base to be assigned, step 14. The next step, step 16, is to correlate the base and template locations; on this first cycle this is a trivial step. A determination is then made as to whether the template molecule is associated with a reporter. That is to say, in step 18 a test is made as to whether the subject template has a reporter or not. If after the sequencing operation the template is associated with a reporter, the procedure moves on to step 20. Here a test is made to determine whether the reporter comes from a previous cycle. If it does not, then it is identified and a new base assigned, step 22. Thus the base has been correctly identified and all is well.

The procedure then moves to step 24 where a test is made as to whether there are any more templates. If so, the procedure repeats from step 18.

If in step 20 it is determined that the reporter associated with the base is from a previous cycle, then no base is assigned, step 26, and the procedure goes straight to step 24 and to the next template, if any.

If in step 18 the template is found not to have a reporter, in step 50 a check is made as to whether the mismatch flag is on. The mismatch flag is activated when the number of consecutive pauses exceeds the predetermined maximum, according to a test made at step 30. If the mismatch flag is not on, the procedure moves to step 28, and a pause P is inserted in the sequence. Also, a pause counter, which monitors the number of consecutive pauses which occur, is incremented by one. A test is the made in step 30 to determine whether the number of consecutive pauses exceeds a predetermined threshold or maximum value. If it does not, the procedure moves to step 24 leaving the pause in the sequence. If the number of consecutive pauses does exceed the predetermined maximum, then the preceding base is scored as mismatched and the mismatch flag is activated, step 32, and the procedure then proceeds to step 24.

The pause indicator serves the function of providing an indication of an unknown base. This may prove to be any one of the bases A, C, G and T, or may in fact prove not to be a base at all. By providing for the possibility of an unknown base the information for that template is not wholly discarded. Rather, it may still be used, for example with reference to a reference sequence, as described in the examples below.

If in step 20 it is determined that the reporter is from a previous cycle, in step 52 a check is made as to whether the mismatch flag is on. If the mismatch flag is not on, then the procedure moves to step 22 and a base is assigned. The procedure than moves to step 24 to determine whether there is another template for processing.

If the mismatch flag is on, at step 54 the previously assigned base is replaced with an IUB code representing all other bases except the one which was mismatched. This is because if the previous base was labelled "C" but is now known to be mismatched, it is clear the base is either A, G or T.

When there are no more templates, the test at step 24 has the result NO, and the procedure moves to step 34, where a determination is made as to whether there are any more cycles to be completed, that is, whether there are any more bases for that molecule. If there are, the procedure moves to the data for the next cycle, step 36, after which the processing proceeds again from step 16, with correlation of the base and template locations.

Eventually the test at step 34 will have the result NO, and that leads to the end of the procedure, step 38.

There may be subsequent processing applied to the sequence as produced by the system of FIG. 1, for example to compare the sequence found by the method with a reference sequence. Examples of this are described below.

The steps shown in FIG. 1, subsequent to the steps 10 to 14 which involve chemical reactions, are implemented on a digital computer such as a personal computer (PC). Two examples are shown in more detail by way of pseudocode in the Appendix to this specification. The first pseudocode assumes that the nucleotides are queried by a mixture of all four bases A, C, G, and T, and the second pseudocode is for use when the four bases are used separately in sequence.

The present invention has many applications, some of which are given here. For example, the sequence of DNA and RNA genomes can be determined using this method. Further, sequence variations in regions of or entire genomes, mRNA representations of regions of or entire genomes or in artificially generated representations of a genome (eg. PCR products of regions of a genome) which result from substitutions, deletions or insertions of one or more bases can be identified.

The present invention has application in haplotyping (determining sequence differences between chromosome pairs in an individual) and also in quantitative mRNA expression analysis, for example in comparing levels of mRNA expression between samples derived from different cell types (tissues) or differently treated cells. This technique may also be applied to identifying sequences derived from pathogen genomes for use in pathogen detection and identification.

Examples are now given of the way specific sequences are handled by the system in such a way as to reduce errors in the determined sequence.

EXAMPLE 1

The following sequence is obtained from a sequencing reaction:

```
GATCGGCTGACCATGGAC1        (Seq. ID No. 1)
``` wherein 1 indicates a T has been incorporated (and 2=C, 3=A, 4=G).

A failure of further extension for the threshold number of cycles results in marking the sequence to indicate that a base has been misincorporated prior to the threshold number of pauses. Here, a 1 (one) indicates that a T has been incorporated prior to a number of pauses above the predetermined threshold level and thus is likely to have been misincorporated. The sequence may therefore be discarded. Referring to FIG. 1, the procedure follows the path 28, 30 for a predetermined number of steps, until a YES is output at step 30, and the preceding base is marked as mismatched in step 32. Instead of a 1, for the other bases 2, 3 or 4 are used, 2 indicating C, 3 indicating A, and 4 indicating G.

EXAMPLE 2

The following sequences are obtained from a sequencing reaction. The first is a newly determined sequence and the second is a reference sequence:

```
GATCGGCTGACCATGGACC1CTGACAGT    (Seq. ID No. 2)

GATCGGCTGACCATGGACCTCTGACAGT    (Seq. ID No. 3)
```

Pausing for longer than the threshold number of cycles marks a 1 for T as a mis-incorporation. In this case, sequencing has resumed after the threshold number of sequences. When the sequence obtained is compared to the reference sequence, sequence alignment demonstrates a T.1 alignment at the paused position. It can therefore be discounted as a real base difference with the reference sequence. The sequence alignment represents a stage additional to the processing illustrated in FIG. 1.

EXAMPLE 3

When a pause is encountered during a sequene, its position is marked as P. If the following new and reference sequences are obtained:

```
GATCGGCTGACCATGGAPCCTCTGACAGT    (Seq. ID No. 4)

GATCGGCTGACCATCGACCTCTGACAGT     (Seq. ID No. 5)
``` sequence alignment with the reference sequence in the presence or absence of a gap at the position marked with a P reveals that it was a pause. All of the sequence is therefore contiguous and useful. The sequence alignment again represents a stage additional to the processing illustrated in FIG. 1.

EXAMPLE 4

The following sequence is obtained in a sequencing reaction:

```
GATCGGCTGACCATGGPCCTCTGACAGT     (Seq. ID No. 6)

GATCGGCTGACCATGGACCTCTGACAGT     (Seq. ID No. 7)
```

The position marked as P is the incorporation of a base with a failed reporter. Sequence alignment with a reference sequence in the presence or absence of a gap at the marked position reveals that this represents a gap in the sequence. The extracted sequence remains useful. In this instance the P can be substituted with an 'N' to signify a gap in the sequence. The sequence alignment again represents a stage additional to the processing illustrated in FIG. 1.

APPENDIX

First Pseudocode
    Example of a pseudo code for sequence assembly after completion of the sequencing reactions.

```
Main( )
{
Locate templates ( );
For (;number of cycles to analyse;);
{
  Correlate reporters with template locations( )
  While (there are templates)
  {
    if (template location does not have a reporter)
    {
      increment pause counter;
          if (pause counter>threshold) mark preceding base
             as a mismatch;
    }
       else if (reporter is from the preceding cycle)discard;
       else identify and assign base to template;
       move to the next template;
  }
     if (more cycles to be analysed) move to data for the
        next sequencing cycle;
     else return;
  }
}
Second Pseudocode
    Pseudocode for sequential single base sequencing
Main( )
{
Locate templates ( );
While (there are cycles)
{
  read data for cycle
For (;four bases;)
{
  Correlate reporters with template locations( )
  While (there are templates)
  {
    if (reporter is from the preceding cycle) discard;
    else identify and assign base to template;
    mark template as extended( );
    next template
  }
     increment pause marker to all templates not
     marked extended( );
  while (paused templates)
  {
     if (number of pauses have reached the threshold) mark
         preceding base as misincorporated
  }
     move to next cycle( );
}
  Output sequence for analysis( );
}
```

---

The invention claimed is:

1. A method for obtaining maximally contiguous nucleic acid sequence from a nucleic acid sequencing reaction wherein an immobilized primer-template complex is extended enzymically utilizing one or more reporter moiety-labelled nucleotides as said enzyme substrate, comprising the steps of:
   a) determining whether said reporter moiety is detectable and corresponds with the location of said primer-template complex;
   b) in the absence of any reporter moiety signal corresponding to the location of the primer-template complex, recording a pause for the corresponding primer-template complex and incrementing a corresponding pause counter;
   c) if the pause counter, incremented for a given primer-template complex, exceeds a predetermined threshold, deeming the base preceding the first of the consecutive pauses a mismatch and marking the base corresponding to that location accordingly in the sequence,
   d) if a reporter moiety is detected following step a), recording the corresponding base and assigning said base to the sequence of the said primer-template complex and setting the pause counter to zero,
   e) eliminating the reporter moiety attached to any incorporated base, and
   f) repeating steps a) to e) until the sequencing reaction is complete.

2. The method of claim 1, wherein the nucleic acid sequence is annotated to mark the locations in the sequence where a reporter moiety was not detected to indicate the potential for a gap in the sequence.

3. The method of claim 1, wherein said signal is rejected if the reporter moiety detected is from the preceding base addition and has failed to eliminate in step e).

4. The method of claim 1, further comprising the step of determining the location of the template by detecting the location of the reporter moiety on the incorporated base.

5. The method of claim 1, further comprising the step of determining the location of the template by detecting the location of a reporter moiety attached to the primer-template complex that is distinguishable from any reporter moiety present on the reporter-labelled base nucleotide.

6. The method of claim 1, wherein the location is determined by the co-location of the reporter moiety on the incorporated labelled base and the reporter moiety attached to the primer-template complex which is distinguishable from those corresponding to the reporter-labelled base nucleotide.

7. The method of claim 1, wherein the primer in the primer-template complex is covalently attached to the template.

8. The method of claim 1, wherein the enzyme is a nucleic acid polymerase.

9. The method of claim 1, wherein the enzyme is a nucleic acid ligase.

10. The method of claim 9, wherein the reaction is performed with enzyme substrates comprising two or more ligated bases.

11. The method of claim 1, wherein the reporter moiety is selected from the group consisting of isotope, radioisotope, enzyme, hapten, fluorophore, chromophore, chemiluminescent group, Raman label and electrochemical label.

12. The method of claim 11, wherein the reporter moiety is a fluorophore.

13. The method of claim 1, wherein the reporter-labelled nucleotide comprises one or more of the bases A, G, C and T.

14. The method of claim 1, wherein the reporter-labelled nucleotide comprise one or more of the bases A, G, C and U.

15. A computer program code on computer readable media for performing all of the steps of claim 1, when said program is run on a computer.

* * * * *